United States Patent [19]
Kobayashi et al.

[11] Patent Number: 5,489,591
[45] Date of Patent: Feb. 6, 1996

[54] S-TRIAZINE DERIVATIVE AND REMEDY FOR ESTROGEN-DEPENDENT DISEASE CONTAINING SAID DERIVATIVE AS EFFECTIVE COMPONENT

[75] Inventors: Hideshi Kobayashi; Toshihiko Komatsu; Seiichi Fukuda; Yoshio Tsuchida; Masanobu Kato; Shinichi Yaguchi; Naohito Ogose; Hajime Ono; Yasuhiro Izumisawa; Masayuki Takahashi; Tsutomu Nakagane, all of Tokyo, Japan

[73] Assignee: Zenyaku Kogyo Kabushiki Kaisha, Tokyo, Japan

[21] Appl. No.: 290,870

[22] PCT Filed: Feb. 26, 1993

[86] PCT No.: PCT/JP93/00240

§ 371 Date: Aug. 29, 1994

§ 102(e) Date: Aug. 29, 1994

[87] PCT Pub. No.: WO93/17009

PCT Pub. Date: Sep. 2, 1993

[30] Foreign Application Priority Data

Feb. 28, 1992 [JP] Japan .................................. 4-078449

[51] Int. Cl.$^6$ ..................... A61K 31/53; C07D 403/04; C07D 403/14; C07D 413/04
[52] U.S. Cl. ................... 514/245; 514/227.8; 514/232.2; 514/236.2; 544/198; 544/113; 544/60; 544/83
[58] Field of Search .................................. 544/198, 113, 544/60, 83; 514/245, 227.8, 232.2, 236.2

[56] References Cited

FOREIGN PATENT DOCUMENTS 56-55302  5/1981  Japan .

*Primary Examiner*—John M. Ford
*Attorney, Agent, or Firm*—Oblon, Spivak, McClelland, Maier & Neustadt

[57] ABSTRACT s-Triazine (1,3,5-triazine) is chemically modified to obtain s-triazine derivative effective for prevention and treatment of estrogen-dependent diseases.

12 Claims, No Drawings

S-TRIAZINE DERIVATIVE AND REMEDY FOR ESTROGEN-DEPENDENT DISEASE CONTAINING SAID DERIVATIVE AS EFFECTIVE COMPONENT

TECHNICAL FIELD

The present invention relates to s-triazine derivatives represented by the formula (I) or pharmaceutically acceptable acid addition salts thereof and remedies for estrogen-dependent diseases containing the derivatives as effective components:

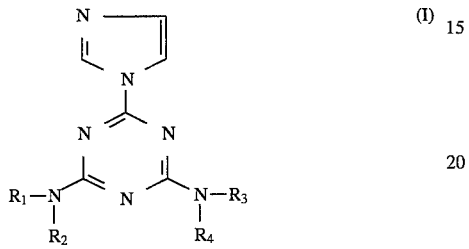

wherein (1) when $R_1$ and $R_2$ are respectively independent and/or $R_3$ and $R_4$ are respectively independent, $R_1$ and $R_3$ represent lower alkyl.

$R_2$ and $R_4$ represent lower alkyl, or phenyl which may be substituted with halogen atom, nitro or amino except for the case where all of $R_1$. $R_2$. $R_3$ and $R_4$ are methyl and (2) when $R_1$ and $R_2$ and/or $R_3$ and $R_4$ are respectively coupled with neighboring nitrogen atom to form cyclic amino group, $NR_1R_2$ represents 1-pyrrolidinyl; piperidino which may be substituted with phenyl; 1-piperazinyl which may be substituted with lower alkyl or phenyl; morpholino; or thiomorpholino, $NR_3R_4$ represents 1-aziridinyl which may be substituted with lower alkyl; 1-pyrrolidinyl which may be substituted with lower alkoxycarbonyl; piperidino which may be mono- or di-substituted with hydroxy, hydroxy lower alkyl, lower alkoxycarbonyl, lower alkyl, cyano, phenyl or ethylenedioxy; 1-piperazinyl which may be substituted with lower alkyl, benzyl, phenyl which in turn may be substituted with halogen atom, nitro or amino, pyridyl or pyrimidinyll morpholino which may be mono- or di-substituted with lower alkyl; 3-thiazolidinyl; thiomorpholino; 1-imidazolyl which may be mono- or di-substituted with lower alkyl; or 1,2,4-triazole-1-yl.

BACKGROUND ART s-Triazine (1,3,5-triazine) derivatives have been researched in the fields of synthetic resins, synthetic fibers and agricultural chemicals and a number of such compounds have been synthesized. In the field of pharmaceuticals, researches have been made with respect to antitumor, antiinflammatory, analgesic and antispasmodic activities. Especially, hexamethylmelamine (HMM) is well-known, which has been developed as analogue of antitumor agent triethylenemelamine (TEM) [B. L. Johnson et al. Cancer, 42:2157–2161 (1978)].

TEM is known as an alkylating agent and is an s-triazine derivative having cytotoxic antitumor activity. HMM has been marketed in Europe under the indications for the treatment of ovarian and small cell lung cancers, and its action on solid cancers has been attractive.

As to its antitumor spectrum and antitumor activity against solid cancers, however, there has been still room for improvement.

DISCLOSURE OF THE INVENTION

The inventors modified s-triazine for the purposes of expanding antitumor spectrum and enhancing antitumor activity of HMM to have surprisedly found out that the compounds represented by the formula (I) exhibit selective aromatase inhibitory activity which has never been reported with respect to conventional s-triazine derivatives, and in addition exhibit cytotoxic antitumor activities comparable to HMM, thus completing the present invention.

The aromatase inhibitory activity is an inhibition of enzymatic conversion from androgens to estrogens in the body. The compounds (I) of the present invention having such inhibitory activity are effective for the treatment of estrogen-dependent diseases such as endometriosis, multicystic ovarium, mastadenoma, endomatrioma and breast cancer.

The terms used for definition of letters in the formula (I) by which the compounds of the present invention are represented are defined and exemplified in the following.

The wording "lower" refers to a group having 1 to 6 carbon atoms unless otherwise indicated.

The "lower alkyl" refers to a straight- or branched-chain alkyl group such as methyl, ethyl, n-propyl, isopropyl, n-butyl, tert-butyl, n-pentyl, n-hexyl or the like.

The "lower alkoxy" refers to a straight- or branched-chain alkoxy group such as methoxy, ethoxy, n-propoxy, isopropoxy, n-butoxy, tert-butoxy, n-pentyloxy, n-hexyloxy or the like.

The "halogen atom" may be fluorine, chlorine, bromine or iodine atom.

The compounds according to the present invention are for example as follows:

2-(1-Imidazolyl)-4-dimethylamino-6-morpholino-1,3,5-triazine 2-(1-Imidazolyl)-4-dimethylamino-6-(1-pyrrolidinyl)-1,3,5-triazine 2-(1-Imidazolyl)-4-dimethylamino-6-piperidino-1,3,5-triazine 2-(1-Imidazolyl)-4-dimethylamino-6-(4-methyl-l-piperazinyl)-1,3,5-triazine 2-(1-Imidazolyl)-4-dimethylamino-6-(4,5-dimethyl-l-imidazolyl)-1,3,5-triazine 2-(1-Imidazolyl)-4-(2-isopropyl-l-imidazolyl)-6-dimethylamino-1,3,5-triazine 2-(1-Imidazolyl)-4-morpholino-6-[4-(2-pyridyl)-l-piperazinyl]-1,3,5-triazine 2-(4-Benzyl-l-piperazinyl)-4-(1-imidazolyl)-6-morpholino-1,3,5-triazine 2-(1-Imidazolyl)-4-(2-methylmorpholino)-6-morpholino-1,3,5-triazine 2-(1-Imidazolyl)-4-(2.6-dimethylmorpholino)-6-morpholino-1,3,5-triazine 2-(1-Imidazolyl)-4-(2,6-dimethylpiperidino)-6-morpholino-1,3,5-triazine 2-(1-Imidazolyl)-4-morpholino-6-(3-thiazolidinyl)-1,3,5-triazine 2-(4,4-Ethylenedioxypiperidino)-4-(1-imidazolyl)-6-morpholino-1,3,5-triazine 2-(4-Cyano-4-phenylpiperidino)-4-(1-imidazolyl)-6-morpholino-1,3,5-triazine
2-(1-Imidazolyl)-4-morpholino-6-(4-phenylpiperidino)-1,3,5-triazine
2-(1-Imidazolyl)-4-(4-phenylpiperidino)-6-thiomorpholino-1,3,5-triazine
2-(4-Ethoxycarbonylpiperidino)-4-(1-imidazolyl)-6-morpholino-1,3,5-triazine
2-(2-tert-Butoxycarbonyl-1-pyrrolidinyl)-4-(1-imidazolyl)-6-morpholino- 1,3,5-triazine
2-(1-Imidazolyl)-4-(2-methyl-1-aziridinyl)-6-morpholino-1,3,5-triazine
2-(4-(4-Fluorophenyl)-1-piperazinyl]-4-(1-imidazolyl)-6-morpholino- 1,3,5-triazine
2-(1-Imidazolyl)-4-morpholino-6-[4-(2-pyrimidinyl)-1-piperazinyl]- 1,3,5-triazine
2-(1-Imidazolyl)-4-morpholino-6-[4-(4-nitrophenyl)-1-piperazinyl]- 1,3,5-triazine
2-(4-(4-Aminophenyl)-1-piperazinyl]-4-(1-imidazolyl)-6-morpholino- 1,3,5-triazine
2-(4-Hydroxypiperidino)-4-(1-imidazolyl)-6-morpholino-1,3,5-triazine
2-(2-(2-Hydroxyethyl)piperidino]-4-(1-imidazolyl)-6-morpholino-1,3,5-triazine
2-(4-(2-Hydroxyethyl)piperidino]-4-(1-imidazolyl)-6-morpholino-1,3,5-triazine
2-(1-Imidazolyl)-4-morpholino-6-thiomorpholino-1,3,5-triazine
2-(1-Imidazolyl)-4-(N-methyl-N-phenylamino)-6-morpholino-1,3,5-triazine
2-(1-Imidazolyl)-4-(N-methyl-N-phenylamino)-6-thiomorpholino-1,3,5-triazine
2-(1-Imidazolyl)-4-dimethylamino-6-(N-methyl-N-phenylamino)-1,3,5-triazine
2-[N-(4-Aminophenyl)-N-methylamino]-4-(1-imidazolyl)-6-morpholino- 1,3,5-triazine
2-(N-Ethyl-N-phenylamino)-4-(1-imidazolyl)-6-morpholino-1,3,5-triazine
2-(N-n-Butyl-N-phenylamino)-4,6-bis(1-imidazolyl)-1,3,5-triazine
2-(N-n-Butyl-N-phenylamino)-4-(1-imidazolyl)-6-morpholino-1,3,5-triazine
2,4-Bis(1-imidazolyl)-6-[N-methyl-N-(4-nitrophenyl)amino]-1,3,5-triazine
2-(1-Imidazolyl)-4-[N-methyl-N-(4-nitrophenyl)amino]-6-morpholino- 1,3,5-triazine
2-[N-(4-Chlorophenyl)-N-methylamino]-4,6-bis(1-imidazolyl)-1,3,5-triazine
2-[N-(4-Chlorophenyl)-N-methylamino]-4-(1-imidazolyl)-6-morpholino- 1,3,5-triazine
2-(1-Imidazolyl)-4-dimethylamino-6-(1H-1,2,4-triazole-1-yl)-1,3,5-triazine
2-(1-Imidazolyl)-4,6-dimorpholino-1,3,5-triazine
2-(1-Imidazolyl)-4,6-bis(1-pyrrolidinyl)-1,3,5-triazine
2-(1-Imidazolyl)-4,6-dipiperidino-1,3,5-triazine
2-(1-Imidazolyl)-4,6-bis(4-phenylpiperidino)-1,3,5-triazine
2-(1-Imidazolyl)-4,6-bis(4-phenyl-1-piperazinyl)-1,3,5-triazine
2-(1-Imidazolyl)-4,6-bis(thiomorpholino)-1,3,5-triazine
2,4-Bis(diethylamino)-6-(1-imidazolyl)-1,3,5-triazine
2,4-Bis(di-n-butylamino)-6-(1-imidazolyl)-1,3,5-triazine
2,4-Bis(1-imidazolyl)-6-morpholino-1,3,5-triazine
2,4-Bis(1-imidazolyl)-6-dimethylamino-1,3,5-triazine
2,4-Bis(1-imidazolyl)-6-diethylamino-1,3,5-triazine
2,4-Bis(1-imidazolyl)-6-(1-pyrrolidinyl)-1,3,5-triazine
2,4-Bis(1-imidazolyl)-6-piperidino-1,3,5-triazine
2,4-Bis(1-imidazolyl)-6-(4-phenylpiperidino)-1,3,5-triazine
2,4-Bis(1-imidazolyl)-6-(4-methyl-1-piperazinyl)-1,3,5-triazine
2,4-Bis(1-imidazolyl)-6-(4-phenyl-1-piperazinyl)-1,3,5-triazine
2,4-Bis(1-imidazolyl)-6-thiomorpholino-1,3,5-triazine
2,4-Bis(1-imidazolyl)-6-(N-methyl-N-phenylamino)-1,3,5-triazine
2-(N-Ethyl-N-phenylamino)-4,6-bis(1-imidazolyl)-1,3,5-triazine
2-(Di-n-butylamino)-4,6-bis(1-imidazolyl)-1,3,5-triazine The compounds of the present invention may have asymmetric carbon atoms in their structures. It is to be understood that isomers due to such asymmetric carbon atoms or combination of any of the isomers are included in the category of the compounds of the present invention.

Moreover, the compounds of the present invention may be converted into a pharmaceutically acceptable salt by using an appropriate acid. The appropriate acids which can be used include, for example, inorganic acids such as hydrochloric, sulfuric, hydrobromic, nitric or phosphoric acid, and organic acids such as acetic, oxalic, propionic, glycolic, lactic, pyruvic, malonic, succinic, maleic, fumaric, malic, tartaric, citric, benzoic, cinnamic, methanesulfonic, benzenesulfonic, p-toluenesulfonic or salicylic acid.

Preparation Processes

The compounds of the present invention represented by the formula (I) may be prepared by, as shown in the following reaction formula, using cyanuric chloride (compound(a)) as starting material and reacting it successively with $HNR_1R_2$ (compound(d)), $HNR_3R_4$ (compound(e)) and imidazole.

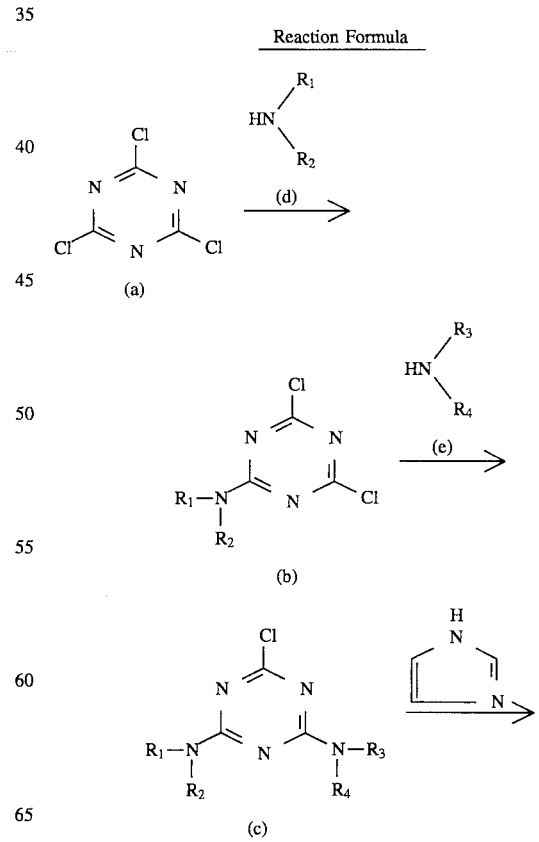

Reaction Formula

-continued
Reaction Formula

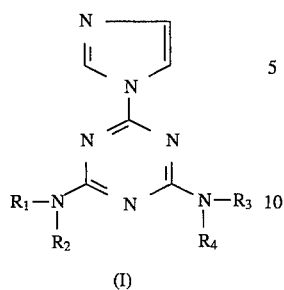

(I)

Now, description will be made on respective preparation processes.

1) Preparation Process (i) of Intermediate (b):

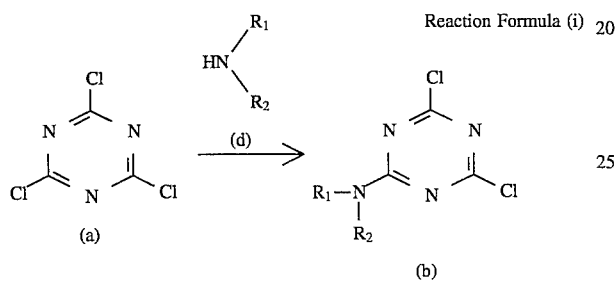

Reaction Formula (i)

In a solvent and under the presence of hydrogen chloride trapping agents, cyanuric chloride (compound (a)) is reacted with secondary amine represented by the formula $HNR_1R_2$ (compound (d)) to obtain an intermediate (b).

The hydrogen chloride trapping agents used in this reaction may be, for example, sodium hydroxide, potassium hydroxide, sodium carbonate, potassium carbonate, triethylamine or pyridine. The solvent used may be, for example, ethylene glycol dimethyl ether, ethyl ether, acetone, toluene, xylene, dioxane, tetrahydrofuran or dichloroethane.

In this reaction, with one molar amount of cyanuric chloride, 0.5–1.2 moles of compound (d) and 0.5–2 moles of hydrogen chloride trapping agents are reacted at the temperature of −15° C.–5° C. for 0.5–2 hours and further at room temperature for 5–50 hours. The secondary amine as compound (d) may be used as hydrogen chloride trapping agents.

2) Preparation Process (ii) of Intermediate (c):

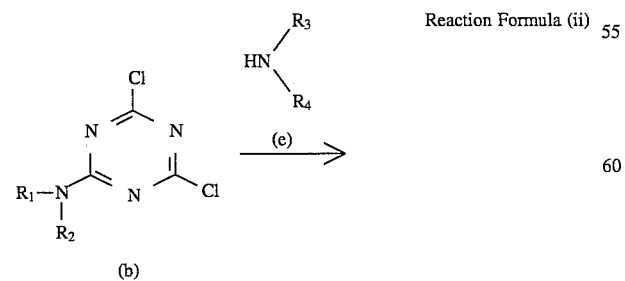

Reaction Formula (ii)

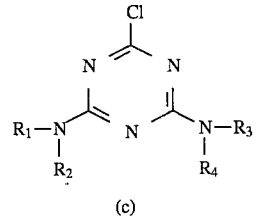

(c)

In a solvent, under the presence of hydrogen chloride trapping agents, the intermediate (b) obtained in the above-mentioned preparation process (i) is reacted with a secondary amine of the formula $HNR_3R_4$ (compound (e)) to obtain an intermediate (c).

The hydrogen chloride trapping agents used in this reaction may be any of those referred to in the above with respect to the preparation process (i). The solvent used may be, for example, N,N-dimethylformamide (DMF), ether, acetone, toluene, xylene, dichloroethane.

In this reaction, with one molar amount of the intermediate (b), 0.5–2 moles of the compound (e) and 0.5–3 moles of hydrogen chloride trapping agents are reacted at −5° C.–0° C. for 0.5–3 hours and further at room temperature for 5 to 50 hours. The secondary amine as compound (e) may be used as hydrogen chloride trapping agents.

3) Preparation Process (iii) of compound (I):

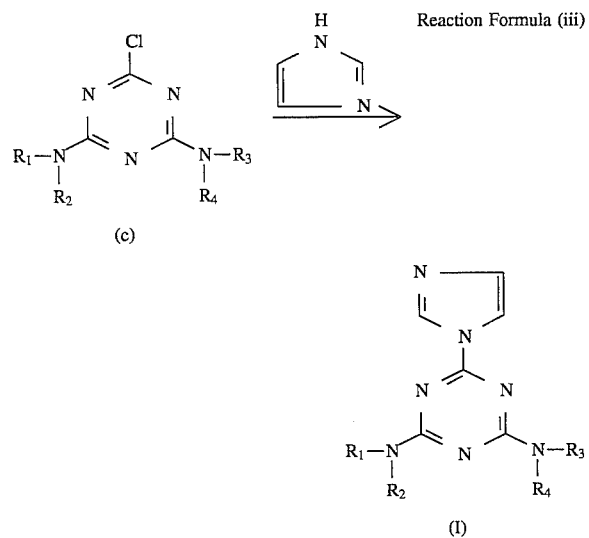

Reaction Formula (iii)

In a solvent, under the presence of hydrogen chloride trapping agents, the intermediate (c) obtained in the above-mentioned preparation process (ii) is reacted with imidazole to obtain the compound (I) of the present invention.

The hydrogen chloride trapping agents used in this reaction may be any of those referred to in the above with respect to the preparation process (i). The solvent used may be, for example, DMF or xylene.

In this reaction, with one molar amount of the intermediate (c), 1– 5 moles of imidazole and 1–5 moles of hydrogen chloride trapping agents are reacted at 80° C.–140° C. for 0.1–5 hours.

When the substituents —$NR_1R_2$ and —$NR_3R_4$ in the compound (I) are the same, the preparation processes (i) and (ii) may be effected at one step to obtain the intermediate (c). In such a case, the reaction conditions are the same as those in the above preparation process (i) except that with one molar amount of compound (a), 2–2.2 moles of compound (d) is reacted at −10° C.–5° C. for 0.1–5 hours and further at room temperature for 3–50 hours.

Likewise, when the substituent —NR$_3$R$_4$ in the compound (I) is 1-imidazolyl, the preparation processes (if) and (iii) may be effected at one step to obtain the compound (I). In such a case, the reaction conditions are the same as those in the preparation process (if) except that with one molar amount of the intermediate (b), 2–4 moles of imidazole is reacted at room temperature to 120° C. for 0.1–50 hours.

The preparation processes (i), (if) and (iii) are interchangeable in order. Obviously, changes of reaction conditions in such interchanges may be effected within abilities of a person skilled in the art.

When either of the substituents —NR$_1$R$_2$ and —NR$_3$R$_4$ in the compound (I) has phenyl substituted with amino, a corresponding compound (I) of the present invention wherein either —NR$_1$R$_2$ or —NR$_3$R$_4$ has phenyl substituted with nitro is used as starting material to readily prepare the compound by conventional method such as catalytic reduction using, for example, platinum oxide.

The resulting products obtained in the above-mentioned respective processes may be purified, as needs demand, by the conventional purification method such as extraction, evaporation, neutralization, filtration, recrystallization or column chromatography.

The compound of the present invention represented by the formula (I) may be converted into pharmaceutically acceptable salt by known various processes. Appropriate acids which may be used include, for example, inorganic acids such as hydrochloric, sulfuric, hydrobromic, nitric or phosphoric acid, and organic acids such as acetic, oxalic, propionic, glycolic, lactic, pyruvic, malonic, succinic, maleic, fumaric, malic, tartaric, citric, benzoic, cinnamic, methanesulfonic, benzenesulfonic, p-toluenesulfonic or salicylic acid.

The pharmacological effects of the compounds of the present invention represented by the formula (I) will now be described:

Nos. of the compounds in the pharmacological tests 1 to 4 correspond to those in Examples referred to hereinafter.

Pharmacological Test 1

Aromatase inhibitory activity was determined according to the method of E. A. Thompson and P. K. Siiteri [J. Biol. Chem., 249, 5364– 5372 (1974)]. The each compound to be tested was added to a reaction vial containing human placenta microsome, [1β,2 β-$^3$H]4-androsten-3,17-dione (3.3 kBq/500 pmol) and NADPH. Inhibitors to be tested had been prepared at concentrations ranging from $1.0 \times 10^{-4}$ to $1.0 \times 10^{-9}$ M. According to this determination method, 4-androsten-3,17-dione was aromatized to generate [$^3$H]H$_2$O which was isolated by treating the reaction mixture with activated charcoal to remove free steroids. The obtained [$^3$H]H$_2$O was measured by a liquid scintillation counter. The measured quantity of [3H]H20 was used to determine aromatase activity, and was compared with the activity when incubated without inhibitor to calculate inhibition ratio (%). Inhibition degree was expressed in the form of [AI-IC$_{50}$(M)] which is concentration of inhibitor required for inhibiting enzymatic activity by 50% in the presence of substrate (4-androsten- 3,17-dione) at concentration of $1.0 \times 10^{-6}$ M.

Pharmacological Test 2

Inhibitory activity against cholesterol side-chain cleaving enzyme was determined according to the method of M. Shikita and P. F. Hall [Proc. Nat. Acad. Sci. U.S.A., 71, 1441 (1974)]. Briefly, the each compound to be tested was added to a reaction vial containing porcine adrenal mitochondria, [4-$^{14}$C]5-cholesten-3β-ol (250 Bq/5 nmol) and NADPH. Inhibitors to be tested had been prepared at concentrations ranging from $1.0 \times 10^{-4}$ to $1.0 \times 10^{-7}$ M. According to this determination method, side-chain cleaving reaction of 5-cholesten-3β-ol) generated 3β-hydroxypregn-5-en-20-one. These were separated by extracting the reaction mixture with methylene-dichloride followed by purifying with thin-layer chromatography. Substrate (5-cholesten-3β-ol) and reaction product (3β-hydroxypregn-5-en-20-one) were respectively measured by a liquid scintillation counter. The measured quantity of 3β-hydroxypregn-5-en-20-one was used to determine cholesterol side-chain cleaving activity which was compared with the activity when incubated without inhibitor to calculate inhibition ratio (%). Inhibition degree was expressed in the form of [SCC-IC$_{50}$(M)] which is concentration of inhibitor required for inhibiting enzymatic activity by 50% in the presence of substrate at concentration of $5.0 \times 10^{-6}$ M.

Results of the pharmacological tests 1 and 2 are shown in Table 1.

TABLE 1

| compound No. | AI-IC$_{50}$(M) | SCC-IC$_{50}$(M) |
| --- | --- | --- |
| 1 | $1.0 \times 10^{-8}$ | $1.0 \times 10^{-4}<$ |
| 2 | $1.3 \times 10^{-6}$ | $1.0 \times 10^{-4}<$ |
| 3 | $7.7 \times 10^{-7}$ | $1.0 \times 10^{-4}<$ |
| 5 | $2.0 \times 10^{-7}$ | $1.0 \times 10^{-4}<$ |
| 6 | $4.3 \times 10^{-6}$ | $1.0 \times 10^{-4}<$ |
| 7 | $6.6 \times 10^{-9}$ | $7.2 \times 10^{-5}$ |
| 8 | $1.1 \times 10^{-8}$ | $5.4 \times 10^{-5}$ |
| 9 | $1.7 \times 10^{-8}$ | $1.5 \times 10^{-5}$ |
| 10 | $3.1 \times 10^{-8}$ | $1.0 \times 10^{-4}<$ |
| 11 | $1.1 \times 10^{-8}$ | $1.9 \times 10^{-5}$ |
| 12 | $2.4 \times 10^{-8}$ | $1.0 \times 10^{-4}<$ |
| 13 | $9.0 \times 10^{-9}$ | $2.2 \times 10^{-5}$ |
| 14 | $6.7 \times 10^{-9}$ | $3.1 \times 10^{-5}$ |
| 16 | $5.3 \times 10^{-9}$ | $1.0 \times 10^{-4}<$ |
| 17 | $3.1 \times 10^{-7}$ | $1.0 \times 10^{-4}<$ |
| 18 | $3.1 \times 10^{-7}$ | $1.0 \times 10^{-4}<$ |
| 21 | $5.1 \times 10^{-9}$ | $1.0 \times 10^{-4}$ |
| 23 | $2.1 \times 10^{-8}$ | $1.0 \times 10^{-4}<$ |
| 24 | $5.5 \times 10^{-7}$ | $8.0 \times 10^{-5}$ |
| 25 | $6.0 \times 10^{-8}$ | $2.5 \times 10^{-5}$ |
| 26 | $6.2 \times 10^{-8}$ | $1.0 \times 10^{-4}<$ |
| 27 | $6.4 \times 10^{-8}$ | $1.0 \times 10^{-4}<$ |
| 28 | $6.2 \times 10^{-8}$ | $9.5 \times 10^{-6}$ |
| 29 | $2.3 \times 10^{-7}$ | $7.5 \times 10^{-5}$ |
| 30 | $2.2 \times 10^{-7}$ | $6.5 \times 10^{-5}$ |
| 31 | $4.3 \times 10^{-8}$ | $1.0 \times 10^{-4}<$ |
| 32 | $2.9 \times 10^{-8}$ | $1.6 \times 10^{-5}$ |
| 36 | $1.4 \times 10^{-8}$ | $1.2 \times 10^{-5}$ |
| 37 | $1.1 \times 10^{-8}$ | $1.0 \times 10^{-4}<$ |
| 38 | $3.8 \times 10^{-8}$ | $2.3 \times 10^{-5}$ |
| 39 | $2.0 \times 10^{-8}$ | $3.7 \times 10^{-5}$ |
| 40 | $2.4 \times 10^{-8}$ | $6.6 \times 10^{-5}$ |
| 41 | $3.7 \times 10^{-8}$ | $1.0 \times 10^{-4}<$ |
| 42 | $5.7 \times 10^{-8}$ | $1.0 \times 10^{-4}<$ |
| 43 | $2.0 \times 10^{-8}$ | $1.0 \times 10^{-4}<$ |
| 44 | $3.3 \times 10^{-8}$ | $1.0 \times 10^{-4}<$ |
| 45 | $7.2 \times 10^{-9}$ | $1.0 \times 10^{-4}<$ |
| 46 | $5.3 \times 10^{-8}$ | $1.0 \times 10^{-4}$ |
| 47 | $4.4 \times 10^{-8}$ | $1.0 \times 10^{-4}<$ |
| 50 | $1.6 \times 10^{-8}$ | $1.5 \times 10^{-5}$ |
| 52 | $1.0 \times 10^{-8}$ | $1.0 \times 10^{-4}<$ |
| 54 | $8.6 \times 10^{-9}$ | $1.9 \times 10^{-5}$ |
| 55 | $7.7 \times 10^{-9}$ | $2.6 \times 10^{-5}$ |
| 56 | $3.2 \times 10^{-8}$ | $1.0 \times 10^{-4}<$ |
| hydrochloride of No. 57 | $3.1 \times 10^{-8}$ | $1.0 \times 10^{-4}<$ |
| HMM | $1.0 \times 10^{-4}<$ | $1.0 \times 10^{-4}<$ |
| AG | $3.8 \times 10^{-5}$ | $6.6 \times 10^{-5}$ |

The above test results revealed that the compounds of the present invention exhibit aromatase inhibitory activity which is not shown by known s-triazine derivatives (HMM). Since their aromatase inhibitory activity was remarkably stronger than their inhibitory activity against cholesterol side-chain cleaving enzyme, the compounds of the present invention were revealed to have excellent selective aromatase inhibitory activity in comparison with aminoglutethimide (AG) which is commercially available medicine having aromatase inhibitory activity.

As is clear from the foregoing, the compounds of the present invention can selectively inhibit a biosynthetic enzyme for estrogen, by which estrogen-dependent diseases can be treated without supplemental administration of corticosteroids which have possibility of causing side effects.

Pharmacological Test 3

Antitumor activity was evaluated by growth inhibition tests of P388 Lymphocytic Leukemia in vitro to have revealed that the compounds (I) of the present invention exhibit IC50 value in a range of $2.0 \times 10^{-4}$ to $5.0 \times 10^{-6}$ M and to have had cytotoxicity substantially comparable to that of hydroxymethylpentamethylmelamine (HMPMM) presumed to be active principle of HMM [J. Dubois et al. Anticancer Research 10:827–832 (1990)].

Pharmacological Test 4

The acute toxicity of the compounds of the present invention was examined by the following method. ICR female mice (five week old, 20 to 22 g of body weight) to which orally administered was the compound of the present invention suspended in distilled water with 1% hydroxypropylcellulose, and $LD_{50}$ value was determined by observation for fourteen days thereafter. Results of the pharmacological test 4 are shown in Table 2.

TABLE 2

| compound No. | $LD_{50}$ (mg/kg) |
| --- | --- |
| 7 | 300–400 |
| 13 | 400< |
| 16 | 200–300 |
| 37 | 400< |
| 38 | 400< |
| 55 | 400< |

The following descriptions are given for the administration routes, pharmaceutical forms and doses when the compounds of the present invention are applied to mammals, especially to human.

The compounds of the present invention may be administered in oral forms such as tablets, coated tablets, powders, granules, capsules, microcapsules, syrups and so on or in non-oral forms such as injections which may include dissolvable freeze-drying form, suppositories and so on. In the preparation of these forms, pharmaceutically acceptable diluent bases, binders, lubricants, disintegrators, suspensions, emulsifiers, antiseptics, stabilizers and dispersing agents, for example, lactose, sucrose, starch, dextrin, crystalline cellulose, kaolin, calcium carbonate, talc, magnesium stearate, distilled water and physiological saline solution may be used.

Although the daily doses of these compounds may be varied according to the conditions, ages or weights of the subjects to be treated, the daily doses to adult humans may fall within the range of 0.5–50 mg and may be divided into two or three portions.

BEST MODE FOR CARRYING OUT THE INVENTION

Examples

The present invention is more specifically illustrated with reference to the following examples. It is to be, however, noted that the present invention is not limited to the examples.

Example 1

2-(1-Imidazolyl)-4-dimethylamino-6-morpholino-1,3,5-triazine (compound 1)

(1) Cyanuric chloride (11.0 g, 59.6 mmol) was dissolved in ethylene glycol dimethyl ether (100 ml), cooled to −5° C. and gradually added dropwise with 50% aqueous dimethylamine solution (10.8 ml, 120 mmol). This reaction mixture was stirred at the same temperature for 2 hours and then stirred at room temperature overnight. The reaction mixture was evaporated under reduced pressure. The residue obtained was added with dichloromethane and water, and then was shaken for mixing. The organic layer was separated, washed with water and dried over anhydrous magnesium sulfate. The solvent was removed to obtain 11.0 g (yield: 95.4%) of 2,4-dichloro-6-dimethylamino-1,3,5-triazine as colorless crystals having melting point of 122.5° C.–123° C.

(2) The obtained 2,4-dichloro-6-dimethylamino-1,3,5-triazine (1.96 g, 10.2 mmol) was dissolved in DMF (20 ml), added with anhydrous potassium carbonate (1.45 g, 10.5 mmol) and cooled to −5° C.–0° C. This mixture was gradually added dropwise with morpholine (0.96 g, 11.0 mmol) dissolved in DMF (5 ml). The reaction mixture was stirred at room temperature for 17 hours and was evaporated under reduced pressure. The residue obtained was added with dichloromethane and water, and then shaken for mixing. The organic layer was separated from the mixture, sufficiently washed with water, dried over anhydrous magnesium sulfate and evaporated. The residue obtained was purified by silica gel column chromatography, using n-hexane and ethyl acetate (8: 2) as eluant, to obtain 1.37 g (yield: 55.4%) of 2-chloro-4-dimethylamino-6-morpholino- 1,3,5-triazine as colorless crystals having melting point of 96° C. – 97° C.

(3) The obtained 2-chloro-4-dimethylamino-6-morpholino-1,3,5-triazine 492mg (2.02 mmol) was dissolved in DMF (20 ml), added with sodium hydroxide (182 mg, 4.55 mmol) and imidazole (308 mg, 4.52 mmol) and stirred at 110° C.–120° C. for 45 minutes. The reaction mixture was evaporated under reduced pressure. The residue obtained was added with dichloromethane and water, and then was shaken for mixing. The organic layer was separated from the mixture, washed with water and dried over anhydrous magnesium sulfate. The solvent was removed under reduced pressure and the residue was purified by silica gel column chromatography, using dichloromethane and methanol (95:5) as eluant, to obtain 508 mg (yield: 91.4%) of the titled compound as colorless crystals.

Melting Point: 156°–158.5° C.

NMR(CDCl$_3$)δ: 3.15(3H, s), 3.20(3H, s), 3.74(4H, t, J=4Hz), 3.85(4H, t, J=4Hz), 7.08 ( 1H, s), 7.77 ( 1H, s), 8.51 ( 1H, s) MS m/z: 275(M$^+$)

In accordance with the procedure of Example 1, the following compounds were obtained from corresponding starting materials.

2-(1-Imidazolyl)-4-dimethylamino-6-(1-pyrrolidinyl)-1,3,5-triazine (compound 2)

Appearance: colorless crystals

Melting Point: 98°–103° C.

NMR(CDCl$_3$)δ: 1.93–1.99(4H, m), 3.17(6H, s), 3.55–3.64(4H, m), 7.07(1H, s), 7.80(1H, s), 8.53(1H, s) MS m/z: 259(M$^+$)

2-( 1-Imidazolyl)-4-dimethylamino-6-piperidino-1,3,5-triazine (compound 3)

Appearance: colorless crystals
Melting Point: 97.5°–99° C.
NMR(CDCl$_3$) δ: 1.52–1.75(6H, m), 3.17(6H, s), 3.80(4H, t, J=5Hz), 7.07(1H, s), 7.79(1H, s), 8.52(1H, s)
MS m/z: 273(M$^+$)

2-(1-Imidazolyl)-4-dimethylamino-6-(4-methyl-1-piperazinyl-1,3,5-triazine (compound 4)
Appearance: colorless crystals
Melting Point: 68°–72° C.
NMR(CDCl$_3$) δ: 2.34(3H, s), 2.45(4H, t, J=5Hz), 3.16(3H,s), 3.19(3H, s), 3.88(4H, t, J=5Hz), 7.07(1H, s), 7.78(1H, s), 8.52(1H, s)
MS m/z: 288(M$^+$)

2-(1-Imidazolyl)-4-dimethylamino-6-(4,5-dimethyl-1-imidazolyl)-1,3,5-triazine (compound 5)
Appearance: colorless crystals
Melting Point: 191°–194° C.
NMR(CDCl$_3$)δ: 2.21(3H, s), 2.54(3H, s), 3.27(3H, s), 3.29(3H, s), 7.15(1H, s), 7.80(1H, s), 8.50(1H, s), 8.56(1H, s)
MS m/z: 284 (M$^+$)

2-(1-Imidazolyl)-4-(2-isopropyl-1-imidazolyl)-6-dimethylamino-1,3,5-triazine (compound 6)
Appearance: colorless crystals
Melting Point: 129.5°–131.5° C.
NMR(CDCl$_3$) δ: 1.43(6H, d, J=7Hz), 3.30(3H, s), 3.32(3H, s), 4.09(1H, sept, J=7Hz), 6.99(1H, s), 7.17(1H, s), 7.82(1H, s), 7.87(1H, s), 8.57(1H, s)
MS m/z: 298(M$^+$)

Example 2

2-(1-Imidazolyl)-4-morpholino-6-(3-thiazolidinyl)-1,3,5-triazine (compound 7)

(1) Cyanuric chloride (7.36 g, 39.9 mmol) was dissolved in acetone (120 ml), cooled to −15° C. and gradually added dropwise with morpholine (7.00 ml, 80.3mmol) dissolved in acetone (20 ml). This reaction mixture was stirred at the same temperature for 30 minutes and then stirred at room temperature overnight. The reaction mixture was evaporated under reduced pressure. The residue was added with dichloromethane and water, and then shaken for mixing. The organic layer was separated from the mixture, washed with water and dried over anhydrous magnesium sulfate. The solvent was removed under reduced pressure and the obtained residue was purified by silica gel column chromatography, using n-hexane and ethyl acetate (8: 2) as eluant, to obtain 6.33 g (yield: 67.5%) of 2,4-dichloro- 6-morpholino-1,3,5-triazine as colorless crystals having melting point of 160.5° C.–161° C.

(2) The obtained 2,4-dichloro-6-morpholino-1,3,5-triazine (237 mg, 1.00 mmol) was dissolved in DMF (3 ml), added with anhydrous potassium carbonate (138 mg, 1.00 mmol) and cooled to −5° C.–0° C. This mixture was gradually added dropwise with thiazolidine (103 mg, 1.15 mmol) dissolved in DMF (1 ml). The reaction mixture was stirred at room temperature overnight and was evaporated under reduced pressure. The residue was added with ethyl acetate and water, and then shaken for mixing. The organic layer was separated from the mixture, washed with water, dried over anhydrous magnesium sulfate and evaporated. The residue obtained was purified by silica gel column chromatography, using n-hexane and ethyl acetate (7:3) as eluant, to obtain 282 mg (yield: 97.2%) of 2-chloro-4-morpholino-6-(3-thiazolidinyl)-1,3,5-triazine having melting point of 137° C.–139.5° C. (3) The obtained 2-chloro-4-morpholino-6-(3-thiazolidinyl)-1,3,5-triazine (85.2 mg, 0.296 mmol) was dissolved in DMF (2 ml), added with sodium hydroxide (23.7 mg, 0.593 mmol) and imidazole (43.4 mg, 0.637 mmol) and stirred at 110° C.–120° C. for 30 minutes. The reaction mixture was evaporated under reduced pressure. The obtained residue was added with ethyl acetate and water, and then shaken for mixing. The organic layer was separated from the mixture, washed with water and dried over anhydrous magnesium sulfate. The solvent was removed under reduced pressure and the residue was purified by silica gel column chromatography, using dichloromethane and methanol (98: 2) as eluant, to obtain 83.7 mg (yield: 88.6%) of the titled compound.

Appearance: colorless crystals
Melting Point: 183°–187° C.
NMR(CDCl$_3$) δ: 3.10(2H, t, J=6.5Hz), 3.74(4H, t, J=4Hz), 3.85(4H, br.s), 3.92–3.99(2H, m), 4.74(2H, br.s), 7.09(1H, s), 7.77(1H, s), 8.50(1H, s)
MS m/z: 319(M$^+$)

In accordance with the procedure of Example 2, the following compounds were obtained from corresponding starting materials.

2-(1-Imidazolyl)-4-morpholino-6-[4-(2-pyridyl)-1-piperazinyl]-1,3,5-triazine (compound 8)
Appearance: colorless crystals
Melting Point: 157.5°–160.5° C.
NMR(CDCl$_3$) δ: 3.63(4H, t, J=5Hz), 3.76(4H, t, J=5Hz), 3.86(4H, d, J=4Hz), 3.97(4H, br.s), 6.65–6.70(2H, m), 7.09(1H, s), 7.49–7.55(1H, m), 7.78(1H, s), 8.21–8.23(1H, m), 8.52(1H, s)
MS m/z: 394 (M+H) $^+$ 2-(4-Benzyl-1-piperazinyl)-4-(1-imidazolyl)-6-morpholino-1,3,5-triazine (compound 9)
Appearance: colorless crystals
Melting Point: 207°–209° C.
NMR(CDCl$_3$) δ: 2.49(4H, br.s), 3.55(2H, s), 3.73(4H, t,J=4.5Hz), 3.83(8H, br.s), 7.07(1H, dd, J=1Hz, 1.5 Hz), 7.25–7.34(5H, m), 7.74(1H, d, J=1.5Hz), 8.48(1H, d, J=1Hz)
MS m/z: 406(M$^+$)

2-(1-Imidazolyl)-4-(2,6-dimethylmorpholino)-6-morpholino-1,3,5-triazine (compound 10: mixture of cis- and trans-forms derived from 2,6-dimethylmorpholino group)
Appearance: colorless crystals
Melting Point: 165.5°–167.5° C. NMR(CDCl$_3$) δ: 1.26(6H, d, J=6Hz), 2.57–2.66(2H, m), 3.55–3.68(2H, m), 3.75(4H, t, J=4Hz), 3.85(4H, br.s), 4.51–4.64(2H, m), 7.09(1H, t, J=1Hz), 7.76(1H, t, J=1Hz), 8.49(1H, t, J=1Hz)
MS m/z: 345(M$^+$)

2-(1-Imidazolyl)-4-(3,5-dimethylpiperidino)-6-morpholino-1,3,5-triazine (compound 11: mixture (1:1) of cis- and trans-forms derived from 3,5-dimethylpiperidino group)
Appearance: colorless crystals
Melting Point: 164°–167° C.
NMR(CDCl$_3$) δ: 0.77–0.87(1H, m), 0.94(3H, d, J=5Hz), 0.95(9H, d, J=6Hz), 1.49(1H, t, J=6Hz), 1.57–1.67(3H, m), 1.83(1H, br.s), 1.87(2H, br.s), 1.95–1.99(1H, m), 2.29(3H, dd, J=12Hz, 20Hz), 3.34–3.56(1H, m), 3.75(8H,t), 3.80–3.85(8H, m), 4.68–4.78(3H, m), 7.08(2H, dd, J=1Hz, 1.5Hz), 7.77(2H, d, J=1.5Hz), 8.50(2H, d, J=1Hz)
MS m/z: 343(M$^+$)

2-(4,4-Ethylenedioxypiperidino)-4-(1-imidazolyl)-6-morpholino-1,3,5-triazine (compound 12)
Appearance: colorless crystals
Melting Point: 174°–176° C.
NMR(CDCl$_3$) δ: 1.74(4H, t, J=6Hz), 3.75(4H, t, J=4Hz), 3.84(4H, br.s), 3.94(4H, br.s), 4.01(4H, s), 7.08(1H, s), 7.76(1H, s), 8.50(1H, s)

MS m/z: 373(M⁺)

2-(4-Cyano-4-phenylpiperidino)-4-(1-imidazolyl)-6-morpholino-1,3,5-triazine (compound 13)
Appearance: colorless crystals
Melting Point: 160°–161.5° C.
NMR(CDCl₃) δ: 2.02(2H, dr, J=4Hz, 13Hz), 2.19–2.25(2H, m), 3.32–3.34(2H, m), 3.76(4H, t, J=4Hz), 3.86(4H, br.s), 4.94–5.07(2H, m), 7.10(1H, t, J=1Hz), 7.32–7.52(5H, m), 7.77(1H, t, J=1Hz), 8.51(1H, t, J=1Hz)
MS m/z: 416(M⁺)

2-(1-Imidazolyl)-4-morpholino-6-thiomorpholino-1,3,5-triazine (compound 37)
Appearance: colorless crystals
Melting Point: 218°–220° C.
NMR(CDCl₃) δ: 2.64–2.69(4H, m), 3.74(4H, t), 3.84(4H, br.s), 4.14(4H, br.s), 7.09(1H, d, J=1Hz), 7.75(1H, d, J=1Hz), 8.49(1H, s)
MS m/z: 333(M⁺)

2-(1-Imidazolyl)-4-morpholino-6-(4-phenylpiperidino)-1,3,5-triazine (compound 38)
Appearance: colorless crystals
Melting Point: 173.5°–175° C.
NMR(CDCl₃) δ: 1.69(2H, dq, J=4Hz, 12Hz), 1.95(2H, br.d, J=12Hz), 2.81(1H, tt, J=4Hz, 12Hz), 2.96(2H, br.t, J=12Hz), 3.76(4H, t, J=4Hz), 3.86(4H, br.s), 4.86–5.06(2H, m), 7.09(1H, t, J=1Hz), 7.78(1H, t, J=1Hz), 7.18–7.25(3H, m), 7.29–7.35(2H, m), 8.52(1H, t, J=1Hz)
MS m/z: 391 (M⁺)

2-(1-Imidazolyl)-4-(4-phenylpiperidino)-6-thiomorpholino-1,3,5-triazine (compound 39)
Appearance: colorless crystals
Melting Point: 177.5°–178.5° C.
NMR(CDCl₃) δ: 1.69(2H, dq, J=4Hz, 12Hz), 1.95(2H, br.d, J=12Hz), 2.67 (4H, t, J=5Hz), 2.81(1H, tt, J=4Hz, 12Hz), 2.95(2H, br.t, J=12Hz), 4.16(4H, br.s), 4.85–5.05(2H, m), 7.09(1H, t, J=1Hz), 7.78(1H, t, J=1Hz), 7.19–7.26(3H, m), 7.29–7.36(2H, m), 8.52(1H, t, J=1Hz)
MS m/z: 407(M⁺)

2-(4-Ethoxycarbonylpiperidino)-4-(1-imidazolyl)-6-morpholino-1,3,5-triazine (compound 40)
Appearance: colorless crystals
Melting Point: 44°–46° C.
NMR(CDCl₃) δ: 1.26(3H, t, J=7Hz), 1.71(2H, dq, J=4Hz, 11Hz), 1.98(2H, br.d, J=11Hz), 2.59(1H, tt, J=4Hz, 11Hz), 3.09(2H, br.t, J=11Hz), 3.74(4H, t, J=4Hz), 3.84(4H, br.s), 4.16(2H, q, J=7Hz), 4.53–4.73(2H, m), 7.08(1H, d, J=1Hz), 7.76(1H, d, J=1Hz), 8.49(1H, s)
MS m/z: 387(M⁺)

2-(2-tert-Butoxycarbonyl-1-pyrrolidinyl)-4-(1-imidazolyl)-6-morpholino-1,3,5-triazine (compound 41)
Appearance: colorless crystals
Melting Point: 160°–163° C.
NMR(CDCl₃) δ: 1.42 (9H, s), 1.91–2.14(3H, m), 2.25–2.34(1H, m), 3.61–3.85(10H, m), 4.38–4.52(1H, m), 7.07(1H,s), 7.58(1H, s), 8.49(1H, s)
MS m/z: 401 (M⁺)

2-(1-Imidazolyl)-4-(2-methyl-1-aziridinyl)-6-morpholino-1,3,5-triazine (compound 42)
Appearance: colorless crystals
Melting Point: 142.5°–144° C.
NMR(CDCl₃) δ: 1.40(3H, d, J=5.5Hz), 2.20(1H, d, J=4Hz), 2.47(1H, d, J=5.5Hz), 2.64(1H, d quint, J=4Hz, 5.5Hz), 3.76(4H, t, J=4Hz), 3.90(4H, t, J=4Hz), 7.10(1H, d, J=1Hz), 7.79(1H, d, J=1Hz), 8.54(1H, s)
MS m/z: 287(M⁺)

2-[4-(4-Fluorophenyl)-1-piperazinyl]-4-(1-imidazolyl)-6-morpholino-1,3,5-triazine (compound 43)
Appearance: colorless crystals
Melting Point: 177°–179° C.
NMR(CDCl₃) δ: 3.14(4H, t, J=5Hz), 3.75(4H, t, J=4Hz), 3.86(4H, br.s), 4.01(4H, br.s), 6.89–7.03(4H, m), 7.09(1H, t, J=1Hz), 7.77(1H, t, J=1Hz), 8.51 (1H, t, J= 1Hz)
MS m/z: 410(M⁺)

2-(1-Imidazolyl)-4-morpholino-6-[4-(2-pyrimidinyl)-1-piperazinyl]-1,3,5-triazine (compound 44)
Appearance: colorless crystals
Melting Point: 183°–185° C.
NMR(CDCl₃) δ: 3.76(4H, t, J=4Hz), 3.86–3.92(12H, br.s), 6.54(1H, t, J=5Hz), 7.10(1H, t, J=1Hz), 7.78(1H, t, J=1Hz), 8.34(2H, d, J=5Hz), 8.52(1H, t, J=1Hz)
MS m/z: 394 (M⁺)

2-(1-Imidazolyl)-4-morpholino-6-[4-(4-nitrophenyl)-1-piperazinyl]-1,3,5-triazine (compound 45)
Appearance: yellow crystals
Melting Point: 282°–284° C.
NMR(CDCl₃) δ: 3.53(4H, t, J=5Hz), 3.76(4H, t, J=4Hz), 3.87(4H, br.s), 4.03(4H, br.s), 6.85(2H, d, J=9Hz), 7.10(1H, t, J=1Hz), 7.77(1H, t, J=1Hz), 8.16(2H, d, J=9Hz), 8.51(1H, t, J=1Hz)
MS m/z: 437(M⁺)

2-(4-Hydroxypiperidino)-4-(1-imidazolyl)-6-morpholino-1,3,5-triazine (compound 46)
Appearance: colorless crystals
Melting Point: 184°–185° C.
NMR(CDCl₃) δ: 1.49–1.63(2H, m), 1.92–1.99(2H, m), 2.20(1H, br.s), 3.42(2H, br.t, J=8Hz), 3.75(4H, t, J=5Hz), 3.85(4H, t, J=5Hz), 3.99(1H, tt, J=4Hz, 8Hz), 4.25–4.42(2H, m), 7.08(1H, t, J=1Hz), 7.77(1H, t, J=1Hz), 8.50(1H, t, J=1Hz)
MS m/z: 331 (M⁺)

2-[2-(2-Hydroxyethyl)piperidino]-4-(1-imidazolyl)-6-morpholino-1,3,5-triazine (compound 47)
Appearance: colorless crystals
Melting Point: 176.5°–178° C.
NMR(CDCl₃) δ:0.88(1H, t, J=7Hz), 1.23–1.31(1H, m), 1.42–1.62(1H, m), 1.65–1.81(5H, m), 2.14(1H, br.t, J=13Hz), 2.80(1H, dr, J=3Hz, 13Hz), 3.30–3.43(1H, m), 3.58–3.86(9H, m), 4.73–4.86(1H, m), 4.87–5.09(1H, m), 7.08(1H, s), 7.75(1H, s), 8.49(1H, s)
MS m/z: 359(M⁺)

2-[4-(2-Hydroxyethyl)piperidino]-4-(1-imidazolyl)-6-morpholino-1,3,5-triazine (compound 48)
Appearance: colorless crystals
Melting Point: 162.5°–164° C.
NMR(CDCl₃) δ: 1.19(2H, dq, J=2Hz, 9Hz), 1.55(2H, q, J=6Hz), 1.70–1.84(3H, m), 2.87(2H, br.t, J=12Hz), 3.72–3.77(6H, m), 3.84(4H, br.s), 4.67–4.87(2H, m), 7.07(1H, d, J=1Hz), 7.75(1H, d, J=1Hz), 8.50(1H, s)
MS m/z: 359(M⁺)

Example 3

2-(1-Imidazolyl)-4-(N-methyl-N-phenylamino)-6-morpholino-1,3,5-triazine (compound 14)

(1) Cyanuric chloride (7.30 g, 39.6 mmol) was dissolved in toluene (100 ml), cooled to −15° C., added with anhydrous sodium carbonate (4.19 g, 39.6 mmol), stirred for 10 minutes and gradually added dropwise with N-methylaniline (4.24 g, 39.2 mmol) dissolved in toluene (50 ml). This reaction mixture was stirred at the same temperature for 30 minutes and then stirred at room temperature overnight. The reaction mixture was evaporated under reduced pressure. The residue was added with dichloromethane and water, and then shaken for mixing. The organic layer was separated from the mixture, washed with water and dried over anhydrous magnesium sulfate. The solvent was removed under reduced pressure and the obtained residue was purified by silica gel column chromatography, using n-hexane and ethyl acetate (4: 1) as eluant, to obtain 6.13 g (yield: 60.6%) of 2,4-dichloro-6-(N-methyl-N-phenylamino)- 1,3,5-triazine as colorless crystals having melting point of 131.5° C.–132.5° C.

(2) The obtained 2,4-dichloro-6-(N-methyl-N-phenylamino)-1,3,5-triazine (956 mg, 3.75mmol) was dissolved in DMF (10 ml), added with anhydrous potassium carbonate (518 mg, 3.77 mmol), cooled to –5° C.–0° C. and gradually added dropwise with morpholine (359 mg, 4.13 mmol) dissolved in DMF (5 ml). The reaction mixture was stirred at room temperature for 24 hours and evaporated under reduced pressure. The residue was added with ethyl acetate and shaken for mixing. The organic layer was separated from the mixture, washed with water and dried over anhydrous magnesium sulfate. The solvent was removed under reduced pressure and the obtained residue was purified by silica gel column chromatography, using dichloromethane and ethyl acetate (20:1) as eluant, to obtain 958 mg (yield: 83.5%) of 2-chloro-4-(N-methyl-N-phenylamino)- 6-morpholino-1,3,5-triazine as colorless crystals having melting point of 93.5° C.–95.5° C.

(3) The obtained 2-chloro-4-(N-methyl-N-phenylamino)-6-morpholino- 1,3,5-triazine (135 mg, 0.457 mmol) was dissolved in DMF (5 ml), added with sodium hydroxide (19.2 mg, 0.480 mmol) and imidazole (32.7 mg, 0.480 mmol) and stirred at 110° C.–120° C. for 5 hours. After allowing to cool to room temperature, the solvent was removed under reduced pressure. The residue was added with ethyl acetate and water, and then shaken for mixing. The organic layer was separated from the mixture, washed with water and dried over anhydrous magnesium sulfate. The solvent was removed under reduced pressure and the residue was purified by silica gel column chromatography, using dichloromethane and methanol (20:1) as eluant, to obtain 71.3 mg (yield: 52.8%) of the titled compound as colorless crystals.

Melting Point: 119°–120.5° C.
NMR(CDCl$_3$) δ: 3.54(3H, s), 3.7–3.8(8H, m), 7.04(1H, s), 7.2–7.3(3H, m), 7.3–7.4(2H, m), 7.65(1H, br.s), 8.39(1H, br.s)
MS m/z: 337(M$^+$)

In accordance with the procedure of Example 3, the following compounds were obtained from corresponding starting materials.

2-(1-Imidazolyl)-4-dimethylamino-6-(N-methyl-N-phenylamino)-1,3,5-triazine (compound 33)
Appearance: colorless crystals
Melting Point: 84.5°–86.5° C.
NMR(CDCl$_3$) δ: 3.1(3H, br.s), 3.2(3H, br.s), 3.55(3H, s), 7.04(1H, s), 7.1–7.4(5H, m), 7.68(1H, s), 8.41(1H, s)
MS m/z: 295(M$^+$)

2-(N-Ethyl-N-phenylamino)-4-(1-imidazolyl)-6-morpholino-1,3,5-triazine (compound 49)
Appearance: colorless crystals
Melting Point: 122.5°–123.5° C.
NMR(CDCl$_3$) δ: 1.25(3H, t, J=7Hz), 3.72(6H, br.s), 3.84(2H, br.s), 4.03(2H, q, J=7Hz), 7.03(1H, s), 7.23–7.31(3H, m), 7.38–7.43(2H, m), 7.64(1H, br.s), 8.36(1H,br.s)
MS m/z: 351 (M$^+$)

2-(N-n-Butyl-N-phenylamino)-4,6-bis (1-imidazolyl)-1,3,5-triazine (compound 50)
Appearance: colorless crystals
Melting Point: 79°–81° C.
NMR(CDCl$_3$) δ: 0.97(3H, t, J=7Hz), 1.41(2H, sext, J=7Hz), 1.71(2H, quint, J=7Hz), 4.08(2H, t, J=7Hz), 7.04 (1H, s), 7.20(1H, s), 7.25–7.28(2H, m) 7.38–7.42(2H, m), 7.46–7.53(2H, m), 7.52(1H, s), 7.87(1H, s), 8.27(1H, s), 8.64(1H, s)
MS m/z: 360 (M$^+$)

2-(N-n-Butyl-N-phenylamino)-4-(1-imidazolyl)-6-morpholino-1,3,5-triazine (compound 51)
Appearance: colorless crystals
Melting Point: 105°–106.5° C.
NMR(CDCl$_3$) δ: 0.93(3H, t, J=7Hz), 1.36(2H, sext, J=7Hz), 1.64(2H, quint, J=7Hz), 3.73 (4H, br. s), 3.85(4H, br.s), 3.98(2H, t, J=7Hz), 7.04(1H, br.s), 7.23–7.31 (3H, m), 7.38–7.42(2H, m), 7.68(1H, br.s), 8.46(1H, br.s)
MS m/z: 379(M$^+$)

2,4-Bis(1-imidazolyl)-6-[N-methyl-N-(4-nitrophenyl)amino]-1,3,5-triazine (compound 52)
Appearance: yellow crystals
Melting Point: >250° C.
NMR(CDCl$_3$) δ: 3.74(3H, s), 7.16(2H, s), 7.58(2H, d, J=7Hz), 7.74(2H, br.s), 8.36(2H, d, J=7Hz), 8.52(2H, br.s)
MS m/z: 363(M$^+$)

2-(1-Imidazolyl)-4-[N-methyl-N-(4-nitrophenyl)amino]-6-morpholino- 1,3,5-triazine (compound 53)
Appearance: yellow crystals
Melting Point: 255°–256.5° C.
NMR(CDCl$_3$) δ: 3.62(3H, s), 3.75(6H, br.s), 3.85(2H, br.s), 7.08(1H, s), 7.55(2H, d, J=7Hz), 7.67(1H, s), 8.27(2H, d, J=7Hz), 8.43(1H, s)
MS m/z: 382 (M$^+$)

2-[N-(4-Chlorophenyl)-N-methylamino]-4,6-bis(1-imidazolyl)-1,3,5-triazine (compound 54)
Appearance: colorless crystals
Melting Point: 227°–228° C.
NMR(CDCl$_3$) δ: 3.64(3H, s), 7.09(1H, s), 7.20(1H, s), 7.27(2H, d, J=9Hz), 7.45(2H, d, J=9Hz), 7.57(1H, s), 7.89(1H, s), 8.35(1H, s), 8.65(1H, s)
MS m/z:352(M$^+$)

2-[N-(4-Chlorophenyl)-N-methylamino]-4-(1-imidazolyl)-6-morpholino- 1,3,5-triazine (compound 55)
Appearance: colorless crystals
Melting Point: 167.5°–169° C.
NMR(CDCl$_3$) δ: 3.52(3H, s), 3.73(6H, br.s), 3.85(2H, br.s), 7.06(1H, s), 7.25(2H, d, J=7Hz), 7.37(1H, s), 7.66(2H, d, J=7Hz), 8.40(1H, s)
MS m/z:371 (M$^+$)

Example 4

2-(1-Imidazolyl)-4-dimethylamino-6-(1H-1,2,4-triazole-1-yl)- 1,3,5-triazine (compound 15)

(1) Cyanuric chloride (11.0 g, 59.6 mmol) was dissolved in ethylene glycol dimethyl ether (100 ml), cooled to –5° C. and gradually added dropwise with 50% aqueous dimethylamine solution (10.8 ml, 120 mmol). This reaction mixture was stirred at the same temperature for 2 hours and then stirred at room temperature overnight. The reaction mixture was evaporated under reduced pressure. The obtained residue was added with dichloromethane and water, and then shaken for mixing. The organic layer was separated from the mixture, washed with water and dried over anhydrous magnesium sulfate. The solvent was removed to obtain 11.0 g (yield: 95.4%) of 2,4-dichloro-6-dimethylamino-1,3,5-triazine as colorless crystals having melting point of 122.5° C.–123° C. (2) The obtained 2,4-dichloro-6-dimethylamino-1,3,5-triazine (1.93 g, 10.0 mmol) was dissolved in DMF (8 ml), added with anhydrous potassium carbonate (1.40 g, 10.1 mmol) and cooled to −5° C.–0° C. This mixture was gradually added with imidazole (695 mg, 10.2 mmol). The reaction mixture was stirred at room temperature overnight and evaporated under reduced pressure. The residue was added with ethyl acetate and water, and then shaken for mixing. The organic layer was separated from the mixture, washed with water, dried over anhydrous magnesium sulfate and evaporated. The obtained residue was purified by silica gel column chromatography, using ethyl acetate and methanol (95:5) as eluant, to obtain 873 g (yield: 38.8%) of 2-chloro-4-(1-imidazolyl)-6-dimethylamino- 1,3,5-triazine as colorless crystals having melting point of 88° C.–92° C.

(3) The obtained 2-chloro-4-(1-imidazolyl)-6-dimethylamino-1,3,5-triazine (113 mg, 0.503 mmol) was dissolved in DMF (1 ml), added with 1,2,4-triazole (149 mg, 2.15 mmol) and stirred at 110° C.–120° C. for 4 hours. The reaction mixture was evaporated under reduced pressure. The obtained residue was added with ethyl acetate and water, and then shaken for mixing. The organic layer was separated from the mixture, washed with water and dried over anhydrous magnesium sulfate. The solvent was removed under reduced pressure and the obtained residue was purified by silica gel column chromatography, using ethyl acetate and methanol (9:1) as eluant, to obtain 22.7 mg (yield: 17.6%) of the titled compound as colorless crystals.

Melting Point: 173.5°–177° C.
NMR(CDCl$_3$) δ: 3.35(3H, s), 3.38(3H, s), 7.17(1H, s), 7.88(1H, s), 8.19(1H, s), 8.63(1H, s), 9.24(1H, s)
MS m/z: 257 (M$^+$)

Example 5

2-(1-Imidazolyl)-4,6-dimorpholino-1,3,5-triazine (compound 16)

(1) Cyanuric chloride (3.63 g, 19.7 mmol) was dissolved in ethylene glycol dimethyl ether (50 ml), cooled to −10° C.–0° C. and gradually added dropwise with morpholine (7.00 ml, 80.3 mmol) dissolved in ethylene glycol dimethyl ether (27 ml). This reaction mixture was stirred at the same temperature for 30 minutes and then stirred at room temperature overnight. The reaction mixture was evaporated under reduced pressure. The residue was added with dichloromethane and water, and then shaken for mixing. The organic layer was separated from the mixture, washed with water and dried over anhydrous magnesium sulfate. The solvent was removed under reduced pressure and the obtained residue was purified by silica gel column chromatography, using dichloromethane and ethyl acetate (8:2) as eluant, to obtain 5.13 g (yield: 91.2%) of 2-chloro- 4,6-dimorpholino-1,3,5-triazine as colorless crystals having melting point of 173.5° C.–174° C.

(2) The obtained 2-chloro-4,6-dimorpholino-1,3,5-triazine (1.44 g, 5.04 mol) was dissolved in DMF (40 ml), added with sodium hydroxide (430 mg, 10.2 mmol) and imidazole (694 mg, 10.2 mmol) and stirred at 110° C. –120° C. for 30 minutes. The reaction mixture was evaporated under reduced pressure. The residue was added with ethyl acetate and water, and then shaken for mixing. The organic layer was separated, washed with water, dried over anhydrous magnesium sulfate and evaporated. The obtained residue was recrystallized from ethanol to obtain 1.37 g (yield: 85.1%) of the titled compound as colorless crystals.

Melting Point: 248.5°–249.5° C.
NMR(CDCl$_3$) δ: 3.74(8H, t, J=5Hz), 3.85(8H, br.s), 7.09(1H, s), 7.75(1H, s), 8.49(1H, s)
MS m/z: 317(M$^+$)

In accordance with the procedure of Example 5, the following compounds were obtained from corresponding starting materials.

2-(1-Imidazolyl)-4,6-bis(1-pyrrolidinyl)-1,3,5-triazine (compound 17)
Appearance: colorless crystals
Melting Point: 162°–163.5° C.
NMR(CDCl$_3$) δ: 1.92–1.98(8H, m), 3.56–3.61(8H, m), 7.07(1H, s), 7.80(1H, s), 8.53(1H, s)
MS m/z: 285(M$^+$)

2-(1-Imidazolyl)-4,6-dipiperidino-1,3,5-triazine (compound 18)
Appearance: colorless crystals
Melting Point: 151°–156° C.
NMR(CDCl$_3$) δ: 1.39–1.68(12H, m), 3.71(8H, br.s), 7.00 (1H, s), 7.71(1H, s), 8.44(1H, s)
MS m/z: 313(M$^+$)

2-(1-Imidazolyl)-4,6-bis (4-phenylpiperidino)-1,3,5-triazine (compound 19)
Appearance: colorless crystals
Melting Point: 231°–232° C.
NMR(CDCl$_3$) δ: 1.70–1.80(4H, m), 1.95–2.01(4H, m), 2.83–3.04(6H, m), 4.99–5.04(4H, m), 7.11(1H, s), 7.24–7.29 (6H, m), 7.32–7.38(4H, m), 7.84(1H, s), 8.57(1H, s)
MS m/z: 466 (M+H)$^+$ 2-(1-Imidazolyl)-4,6-bis(4-phenyl-1-piperazinyl)-1,3,5-triazine (compound 20)
Appearance: colorless crystals
Melting Point: 202°–205° C.
NMR(CDCl$_3$) δ: 3.25(8H, t, J=5Hz), 4.03(8H, br.s), 6.89–7.00(6H, m), 7.10(1H, s), 7.27–7.34(4H, m), 7.80(1H, s), 8.54(1H, s)
MS m/z: 467(M$^+$)

2-(1-Imidazolyl)-4,6-bis(thiomorpholino)-1,3,5-triazine (compound 21 )
Appearance: colorless crystals
Melting Point: 239°–241° C.
NMR(CDCl$_3$) δ: 2.66(8H, t, J=5Hz), 4.14(8H, br.s), 7.09(1H, d, J=1Hz), 7.75(1H, d, J=1Hz), 8.49(1H, s)
MS m/z: 349(M$^+$)

2,4-Bis (diethylamino)-6-(1-imidazolyl)-1,3,5-triazine (compound 22)
Appearance: colorless oil
NMR(CDCl$_3$) δ: 1.20(12H, t, J=7Hz), 3.59(4H, q, J=7Hz), 3.61(4H, q, J=7Hz), 7.07(1H, s), 7.79(1H, s), 8.53(1H,s)
MS m/z: 289(M$^+$)

2,4-Bis(di-n-butylamino)-6-(1-imidazolyl)-1,3,5-triazine (compound 34)
Appearance: colorless oil
NMR(CDCl$_3$) δ:0.94(6H, t, J=7Hz), 0.96(6H, t, J=7Hz), 1.33(4H, sext, J=7Hz), 1.36(4H, sext, J=7Hz), 1.64(8H, quint, J=7Hz), 3.49(4H, t, J=7Hz), 3.54(4H, t, J=7Hz), 7.07(1H, t, J=1Hz), 7.76(1H, t, J=1Hz), 8.50 (1H, t, J: 1Hz)
MS m/z: 401 (M$^+$)

Example 6

2,4-Bis(1-imidazolyl)-6-morpholino-1,3,5-triazine (compound 23)

(1) Cyanuric chloride (7.30 g, 39.6 mmol) was dissolved in ethylene glycol dimethyl ether (100 ml), cooled to −15° C. and gradually added dropwise with morpholine (7.00 ml, 80.3 mmol) dissolved in ethylene glycol dimethyl ether (50 ml). This reaction mixture was stirred at the same temperature for 30 minutes and then stirred at room temperature overnight. The reaction mixture was evaporated under reduced pressure. The residue was added with dichloromethane and water, and then shaken for mixing. The organic layer was separated from the mixture, washed with water and dried over anhydrous magnesium sulfate. The solvent was removed under reduced pressure and the obtained residue was purified by silica gel column chromatography, using n-hexane and ethyl acetate (6:4) as eluant, to obtain 6.32 g (yield: 68.0%) of 2,4-dichloro-6-morpholino-1,3,5-triazine as colorless crystals having melting point of 160.5° C.– 161° C.

(2) The obtained 2,4-dichloro-6-morpholino-1,3,5-triazine (1.17 g, 4.98 mmol) was dissolved in DMF (30 ml), added with anhydrous potassium carbonate (2.91 g, 21.1 mmol) and imidazole (1.43 g, 21.0 mmol) and stirred at room temperature for 17 hours. The reaction mixture was evaporated under reduced pressure. The residue was added with ethyl acetate and water, and then shaken for mixing. The organic layer was separated from the mixture, washed with water and dried over anhydrous magnesium sulfate. The obtained residue was purified by silica gel column chromatography, using dichloromethane and methanol (95:5) as eluant, to obtain 483 mg (yield: 32.6%) of the titled compound as colorless crystals.

Melting Point: 268°–270° C.
NMR(CDCl$_3$) δ: 3.82(4H, t, J=4Hz), 3.99(4H, t, J=4Hz), 7.17(2H, s), 7.82(2H, s), 8.58(2H, s)
MS m/z: 298(M$^+$)

In accordance with the procedure of Example 6, the following compounds were obtained from corresponding starting materials.

2,4-Bis(1-imidazolyl)-6-dimethylamino-1,3,5-triazine (compound 24)
Appearance: colorless crystals
Melting Point: 171°–174° C.
NMR(CDCl$_3$) δ: 3.31(6H, s), 7.16(2H, s), 7.83(2H, s), 8.59(2H, s)
MS m/z: 256(M$^+$)

2,4-Bis(1-imidazolyl)-6-diethylamino-1,3,5-triazine (compound 25)
Appearance: colorless crystals
Melting Point: 53°–55° C.
NMR(CDCl$_3$) δ: 1.29(6H, t, J=7Hz), 3.72(4H, q, J=7Hz), 7.16(2H, dd, J=1Hz, 1.5Hz), 7.84(2H, dd, J=1Hz, 1.5Hz), 8.59(2H, t, J=1Hz)
MS m/z: 284(M$^+$)

2,4-Bis(1-imidazolyl)-6-(1-pyrrolidinyl)-1,3,5-triazine (compound 26)
Appearance: colorless crystals
Melting Point: 198.5°–201.5° C.
NMR(CDCl$_3$) δ: 2.02–2.11(4H, m), 3.65–3.76(4H, m), 7.15(2H, s), 7.83(2H, s), 8.58(2H, s)
MS m/z: 282(M$^+$)

2,4-Bis(1-imidazolyl)-6-piperidino-1,3,5-triazine (compound 27)
Appearance: colorless crystals
Melting Point: 208°–211° C.
NMR(CDCl$_3$) δ: 1.62–1.89(6H, m), 3.92(4H, t, J=5Hz), 7.15(2H, s), 7.83(2H, s), 8.58(2H, s)
MS m/z: 296(M$^+$)

2,4-Bis(1-imidazolyl)-6-(4-phenylpiperidino)-1,3,5-triazine (compound 28)
Appearance: colorless crystals
Melting Point: 166.5°–170° C.
NMR(CDCl$_3$) δ: 1.75–1.85(2H, m), 2.05–2.11(2H, m), 2.88–2.97(1H, m), 3.09–3.19(2H, m), 5.04–5.09(2H, m), 7.18 (2H, s), 7.23–7.39(5H, m), 7.86(2H, s), 8.62(2H, s)
MS m/z: 372(M$^+$)

2,4-Bis (1-imidazolyl)-6-(4-methyl-1-piperazinyl)-1,3,5-triazine (compound 29)
Appearance: colorless crystals
Melting Point: 131.5°–135° C.
NMR(CDCl$_3$) δ:2.40(3H, s), 2.55(4H, t, J=5Hz), 4.02(4H, t, J=5Hz), 7.18(2H, s), 7.85(2H, s), 8.60(2H, s)
MS m/z: 311 (M$^+$)

2,4-Bis(1-imidazolyl)-6-(4-phenyl-1-piperazinyl)-1,3,5-triazine (compound 30)
Appearance: colorless crystals
Melting Point: 184°–186° C.
NMR(CDCl$_3$) δ: 3.31(4H, t, J=5Hz), 4.14(4H, t, J=5Hz), 6.92–7.01(3H, m), 7.17(2H, s), 7.29–7.36(2H, m), 7.84(2H, s), 8.60(2H, s)
MS m/z: 373(M$^+$)

2,4-Bis (1-imidazolyl)-6-thiomorpholino-1,3,5-triazine (compound 31)
Appearance: colorless crystals
Melting Point: 223°–224° C.
NMR(CDCl$_3$) δ:2.76(4H, t, J=5Hz), 4.27(4H, t, J=5Hz), 7.17(2H, s), 7.82(2H, s), 8.58(2H, s)
MS m/z: 314(M$^+$)

2,4-Bis(1-imidazolyl)-6-(N-methyl-N-phenylamino)-1,3,5-triazine (compound 32)
Appearance: colorless crystals
Melting Point: 175°–176° C.
NMR(CDCl$_3$) δ: 3.66(3H, s), 7.06(1H, s), 7.19(1H, s), 7.3–7.4(3H, m), 7.4–7.5(2H, m), 7.56(1H, s), 7.89(1H, s), 8.32(1H, s), 8.65(1H, s)
MS m/z: 318(M$^+$)

2-(N-Ethyl-N-phenylamino)-4,6-bis(1-imidazolyl)-1,3,5-triazine (compound 35)
Appearance: colorless crystals
Melting Point: 103.5°–104.5° C.
NMR(CDCl$_3$) δ: 1.33(3H, t, J=7Hz), 4.13(2H, q, J=7Hz), 7.04(1H, s), 7.20(1H, s), 7.2–7.3(2H, m), 7.4–7.5(4H, m), 7.89(1H, s), 8.28(1H, s), 8.65(1H, s)
MS m/z: 332(M$^+$)

2-(Di-n-butylamino)-4,6-bis(1-imidazolyl)-1,3,5-triazine (compound 36)
Appearance: colorless crystals
Melting Point: 106°–107° C.
NMR(CDCl$_3$) δ: 0.99(6H, t, J=7Hz), 1.41(4H, sext, J=7Hz), 1.62–1.74(4H, m), 3.65(4H, t, J=7.5Hz), 7.16(2H, s), 7.82(2H, s), 8.58(2H, s)
MS m/z: 340(M$^+$)

Example 7

2-[N-(4-Aminophenyl)-N-methylamino]-4-(1-imidazolyl)-6-morpholino- 1,3,5-triazine (compound 56)

2-(1-Imidazolyl)-4-[N-methyl-N-(4-nitrophenyl)amino]-6-morpholino- 1,3,5-triazine (115 mg, 0.30 mmol) was dissolved in acetic acid (10 ml) and was catalytically reduced with platinum oxide at room temperature under normal pressure. The reaction mixture was filtered and was evaporated under reduced pressure. The obtained residue was added with dichloromethane and aqueous solution of saturated sodium bicarbonate, and then was shaken for mixing. The organic layer was separated from the mixture, washed with water, dried over anhydrous magnesium sulfate and evaporated. The obtained residue was purified by silica gel column chromatography, using ethyl acetate as eluant, to obtain 36.5 mg (yield: 34.4%) of the titled compound as colorless crystals.

Melting Point: 183°–186.5° C.

NMR(CDCl₃) δ: 3.47(3H, s), 3.59–3.96(10H, m), 6.69(2H,d, J=8Hz), 7.05(2H, d, J=5Hz), 7.08(1H, br.s), 7.70(1H,br.s), 8.40(1H, br.s)

MS m/z: 352(M⁺)

In accordance with the procedure of Example 7, the following compound was obtained from corresponding starting material.

2-[(4-Aminophenyl)-1-piperazino]-4-(1-imidazolyl)-6-morpholino-1,3,5-triazine (compound 57)

Appearance: colorless crystals
Melting Point: 182°–185° C.
NMR(CDCl₃) δ: 3.06(4H, t, J=5Hz), 3.48(2H, br.s), 3.75(4H, t, J=5Hz), 3.86(4H, br.s), 3.99(4H, br.s), 6.67(2H, d, J=5Hz), 6.84(2H, d, J=8Hz), 7.09(1H, t, J=1Hz), 7.77(1H, t, J=1Hz), 8.51(1H, t, J=1Hz)

MS m/z: 407(M⁺)

Example 8

Hydrochloride of 2-(1-imidazolyl)-4,6-dimorpholino-1,3,5-triazine (compound 16)

2-(1-Imidazolyl)-4,6-dimorpholino-1,3,5-triazine (131 mg, 0.412 mmol) was dissolved in dichloromethane (2 ml), cooled to 0° C.–5° C. and added dropwise with 4N hydrogen chloride/dioxane solution (1.00 ml: corresponding to 4.00 mmol of hydrogen chloride). This reaction mixture was stirred at the same temperature for 30 minutes and then stirred at room temperature for 30 minutes. The reaction mixture was added with petroleum ether and the resultant precipitate was fractionally collected. The precipitate was added with water (30 ml) and filtered to remove water-insoluble material. The filtrate was freeze-dried to obtain 143 mg (yield: 97.9%) of the titled compound as colorless powder.

Melting Point: 246°–250° C.
NMR(D₂O) δ: 3.78(8H, t, J=5Hz), 3.88(8H, br.s), 7.60 (1H, s), 8.24(1H, s), 9.58(1H, s)

In accordance with the procedure of Example 8, the following compounds were obtained from corresponding starting materials.

Hydrochloride of 2,4-bis(1-imidazolyl)-6-dimethylamino-1,3,5-triazine (compound 24)

Melting Point: 194.5°–196° C.
NMR(D₂O) δ: 3.36(6H, s), 7.67(2H, s), 8.40(2H, s), 9.79(2H, s)

Hydrochloride of 2-[4-(4-aminophenyl)-1-piperazinyl]-4-(1-imidazolyl)- 6-morpholino-1,3,5-triazine (compound 57)

Melting Point: 187°–192° C.
NMR(D₂O) δ: 3.35(4H, br.s), 3.80(4H, t, J=5Hz), 3.91 (4H, br.s), 4.07(4H, br.s), 7.25(2H, d, J=9Hz), 7.34(2H, d, J=9Hz), 7.60(1H, s), 8.26(1H, s), 9.58(1H, s)

Example 9

Oxalate of 2,4-bis(di-n-butylamino)-6-(1-imidazolyl)-1,3,5-triazine (compound 34)

2,4-Bis(di-n-butylamino)-6-(1-imidazolyl)-1,3,5-triazine (232 mg, 0.577 mmol) was dissolved in acetone (2 ml), added with oxalic acid (52.5 mg, 0.583 mmol) and stirred at room temperature for 1 hour. The reaction mixture was added with n-hexane and the resultant precipitate was collected by filtration. The precipitate was dried under reduced pressure to obtain 275 mg (yield: 96.7%) of the titled compound as colorless powder.

Melting Point: 121°–123° C.

NMR(CDCl₃) δ:0.96(6H, t, J=7Hz), 0.97(6H, t, J=7Hz), 1.28–1.45(4H, m), 1.55–1.68(4H, m), 3.52(4H, t, J=7.5 Hz), 3.55(4H, t, J=7.5Hz), 7.56(1H, br.s), 7.97(1H, t,J=1Hz), 9.31(1H, br.s)

In accordance with the procedure of Example 9, the following compound was obtained from corresponding starting material.

Oxalate of 2,4-bis(diethylamino)-6-(1-imidazolyl)-1,3,5-triazine (compound 22)

Melting Point: 141°–143° C.
NMR(CDCl₃) δ: 1.22(12H, t, J=7Hz), 3.62(8H, q, J=7Hz), 7.49(1H, s), 8.00(1H, s), 9.26(1H, s), 11.36(1H, br.)

CAPABILITY OF EXPLOITATION IN INDUSTRY

The s-triazine derivative according to the present invention has excellent selective aromatase inhibitory activity and therefore a pharmaceutical composition containing the s-triazine derivative as effective component is effective for prevention and treatment of estrogen-dependent diseases.

We claim:

1. An s-triazine compound having the formula (1) or a pharmaceutically-acceptable acid addition salt thereof:

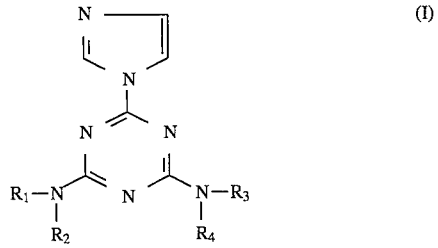

wherein:

(1) when $R_1$ and $R_2$ are independent of each other or $R_3$ and $R_4$ are independent of each other, or both;

$R_1$ and $R_3$ are each lower alkyl;

$R_2$ and $R_4$ are each lower alkyl or phenyl which is unsubstituted or substituted with halogen, nitro or amino;

with the proviso that at least one of $R_2$ or $R_4$ is phenyl which is unsubstituted or substituted with halogen, nitro or amino;

(2) when $R_1$ and $R_2$ or $R_3$ and $R_4$, or both, are, respectively, coupled with an neighboring nitrogen atom to form a cyclic amino group;

$NR_1R_2$ is 1-pyrrolidinyl; piperidino which is unsubstituted or substituted with phenyl; 1-piperazinyl which is unsubstituted or substituted with lower alkyl or phenyl; morpholino; or thiomorpholino;

$NR_3R_4$ is 1-aziridinyl which is unsubstituted or substituted with lower alkyl; 1-pyrrolidinyl which is unsubstituted or substituted with lower alkoxycarbonyl; piperidino which is unsubstituted or mono- or di-substituted with hydroxy, hydroxyl lower alkyl, lower alkoxycarbonyl, lower alkyl, cyano, phenyl or ethylenedioxy; 1-piperazinyl which is unsubstituted or substituted with lower alkyl, benzyl, phenyl which is unsubstituted or substituted with halogen, nitro or amino, pyridyl or pyrimidinyl; morpholino which is unsubstituted or mono- or di-substituted with lower alkyl; 3-thiazolidinyl; thiomorpholino; 1-imidazolyl which is unsubstituted or mono- or di-substituted with lower alkyl; or 1, 2, 4-triazole-1-yl.

2. The compound according to claim 1, wherein $NR_1R_2$ is morpholino or thiomorpholino.

3. The compound according to claim 1, wherein $NR_3R_4$ is morpholino, thiomorpholino or 1-imidazolyl.

4. The compound according to claim 1, wherein $NR_1R_2$ is morpholino or thiomorpholino, and (1) when $R_3$ and $R_4$ are independent of each other, $R_3$ is lower alkyl;

$R_4$ is lower alkyl; or phenyl which is unsubstituted or substituted with halogen, nitro or amino, or (2) when $R_3$ and $R_4$ are coupled to form cyclic amino together with a neighboring nitrogen atom, $NR_3R_4$ is 1-aziridinyl which is unsubstituted or substituted by lower alkyl; 1-pyrrolidinyl which is unsubstituted or substituted with lower alkoxy carbonyl; piperidino which is mono- or di-substituted with hydroxy, hydroxy lower alkyl, lower alkoxycarbonyl, lower alkyl, cyano, phenyl or ethylenedioxy; 1-piperazinyl which is unsubstituted or substituted with benzyl, or phenyl or each of benzyl and phenyl substituted with halogen, nitro, or amino; pyrridyl or pyrimidinyl; morpholino which is unsubstituted or di-substituted with lower alkyl; 3-thiazolidinyl; thiomorpholino; or 1-imidazolyl.

5. The compound according to claim 1, wherein $NR_3R_4$ is morpholino, thiomorpholino or 1-imidazolyl, and (1) when $R_1$ and $R_2$ are independent of each other, $R_1$ is lower alkyl;

$R_2$ is lower alkyl; or phenyl which is unsubstituted or substituted by halogen, nitro or amino, or (2) when $R_1$ and $R_2$ are coupled to form cyclic amino together with a neighboring nitrogen atom, $NR_1R_2$ is 1-pyrrolidinyl; piperidino which is unsubstituted or substituted with phenyl; 1-piperazinyl which is unsubstituted or substituted with lower alkyl or phenyl; morpholino; or thiomorpholino.

6. The compound according to claim 1, wherein said pharmaceutically-acceptable acid addition salt is a salt of an acid selected from the group consisting of hydrochloric, sulfuric, hydrobromic, nitric, phosphoric, acetic, oxalic, propionic, glycolic, lactic, pyruvic, malonic, succinic, maleic, fumaric, malic, tartaric, citric, benzoic, cinnamic, methanesulfonic, benzenesulfonic, p-toluenesulfonic and salicylic acids.

7. A pharmaceutical composition for inhibiting aromatase enzymes, which comprises an effective amount of one or more s-triazine compounds having the formula (I) or a pharmaceutically-acceptable acid addition salt thereof:

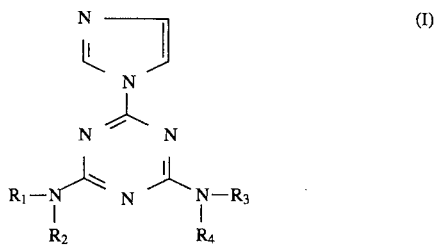

wherein:

(1) when $R_1$ and $R_2$ are independent of each other or $R_3$ and $R_4$ are independent of each other, or both;

$R_1$ and $R_3$ are each lower alkyl;

$R_2$ and $R_4$ are each lower alkyl or phenyl which is unsubstituted or substituted with halogen, nitro or amino;

with the proviso that at least one of $R_2$ or $R_4$ is phenyl which is unsubstituted or substituted with halogen, nitro or amino;

(2) when $R_1$ and $R_2$ or $R_3$ and $R_4$, or both are, respectively, coupled with an neighboring nitrogen atom to form a cyclic amino group;

$NR_1R_2$ is 1-pyrrolidinyl; piperidino which is unsubstituted or substituted with phenyl; 1-piperazinyl which is unsubstituted or substituted with lower alkyl or phenyl; morpholino; or thiomorpholino;

$NR_3R_4$ is 1-aziridinyl which is unsubstituted or substituted with lower alkyl; 1-pyrrolidinyl which is unsubstituted or substituted with lower alkoxycarbonyl; piperidino which is unsubstituted or mono- or di-substituted with hydroxy, hydroxyl lower alkyl, lower alkoxycarbonyl, lower alkyl, cyano, phenyl or ethylenedioxy; 1-piperazinyl which is unsubstituted or substituted with lower alkyl, benzyl, phenyl which is unsubstituted or substituted with halogen, nitro or amino, pyridyl or pyrimidinyl; morpholino which is unsubstituted or mono- or di-substituted with lower alkyl; 3-thiazolidinyl; thiomorpholino; 1-imidazolyl which is unsubstituted or mono- or di-substituted with lower alkyl; or 1, 2, 4-triazole-1-yl and a pharmaceutically acceptable diluent or carrier.

8. The composition according to claim 7, wherein $NR_1R_2$ is morpholino or thiomorpholino.

9. The composition according to claim 7, wherein $NR_3R_4$ is morpholino, thiomorpholino or 1-imidazolyl.

10. The composition according to claim 7, wherein $NR_1R_2$ is morpholino or thiomorpholino, and (1) when $R_3$ and $R_4$ are independent of each other, $R_3$ is lower alkyl;

$R_4$ is lower alkyl; or phenyl which is unsubstituted or substituted with halogen, nitro or amino, or (2) when $R_3$ and $R_4$ are coupled to form cyclic amino together with a neighboring nitrogen atom, $NR_3R_4$ is 1-aziridinyl which is unsubstituted or substituted by lower alkyl; 1-pyrrolidinyl which is unsubstituted or substituted with lower alkoxy carbonyl; piperidino which is mono- or di-substituted with hydroxy, phenyl or ethylenedioxy; 1-piperazinyl which is unsubstituted or substituted with benzyl, or phenyl or each of benzyl and phenyl substituted with halogen, nitro, or amino; pyrridyl or pyrimidinyl; morpholino which is unsubstituted or di-substituted with lower alkyl; 3-thiazolidinyl; thiomorpholino; or 1-imidazolyl.

11. The composition according to claim 7, wherein $NR_3R_4$ is morpholino, thiomorpholino or 1-imidazolyl, and (1) when $R_1$ and $R_2$ are independent of each other, $R_1$ is lower alkyl;

$R_2$ is lower alkyl; or phenyl which is unsubstituted or substituted by halogen, nitro or amino, or (2) when $R_1$ and $R_2$ are coupled to form cyclic amino together with a neighboring nitrogen atom, $NR_1R_2$ is 1-pyrrolidinyl; piperidino which is unsubstituted or substituted with phenyl; 1-piperazinyl which is unsubstituted or substituted with lower alkyl or phenyl; morpholino; or thiomorpholino.

12. The composition according to claim 7, wherein said pharmaceutically-acceptable acid addition salt is a salt of an acid selected from the group consisting of hydrochloric, sulfuric, hydrobromic, nitric, phosphoric, acetic, oxalic, propionic, glycollic, lactic, pyruvic, malonic, succinic, maleic, fumaric, malic, tartaric, citric, benzoic, cinnamic, methanesulfonic, benzenesulfonic, p-toluenesulfonic and salicylic acids.

* * * * *